United States Patent [19]

Hefner, Jr.

[11] Patent Number: 4,489,202

[45] Date of Patent: Dec. 18, 1984

[54] PROCESS FOR PREPARING EPOXY RESINS CONTAINING TRIAZINE GROUPS

[75] Inventor: Robert E. Hefner, Jr., Lake Jackson, Tex.

[73] Assignee: The Dow Chemical Company, Midland, Mich.

[21] Appl. No.: 547,537

[22] Filed: Oct. 31, 1983

[51] Int. Cl.$^3$ .................. C08G 59/06; C08G 59/20
[52] U.S. Cl. ........................... 528/95; 528/92; 528/93; 528/99; 528/119; 252/188.31
[58] Field of Search ............... 528/99, 119, 92, 93, 528/95; 252/188.31

[56] References Cited

U.S. PATENT DOCUMENTS

| | | | |
|---|---|---|---|
| 2,741,607 | 4/1956 | Bradley et al. | 260/248 |
| 2,809,942 | 10/1957 | Cooke, Jr. | 260/2 |
| 2,810,706 | 10/1957 | Frazier et al. | 260/45.5 |
| 2,864,805 | 12/1958 | Cooke, Jr. | 260/47 |
| 2,971,942 | 2/1961 | Masters et al. | 260/2 |
| 3,708,483 | 1/1973 | Anderson et al. | 260/248 CS |
| 4,142,034 | 2/1979 | Schroll | 528/99 |

FOREIGN PATENT DOCUMENTS 56-26925  3/1981  Japan .

*Primary Examiner*—Herbert S. Cockeram
*Attorney, Agent, or Firm*—J. G. Carter

[57] ABSTRACT

Epoxy resins containing triazine groups are prepared by (I) reacting (A) a material having at least one aromatic hydroxyl group per molecule such as bisphenol A with (B) a cyanogen halide such as cyanogen bromide in the presence of (C) a base and recovering a mixture of cyanate-containing products and unreacted (A) materials; (II) trimerizing the product recovered in (I) in the presence of a trimerization catalyst such as cobalt naphthenate and (III) epoxidizing the product from step II by reaction with an epihalohydrin such as epichlorohydrin, dehydrohalogenation of the resultant product with a basic acting material such as sodium hydroxide and recovering the resultant epoxy resin containing triazine groups.

36 Claims, No Drawings

PROCESS FOR PREPARING EPOXY RESINS CONTAINING TRIAZINE GROUPS

BACKGROUND OF THE INVENTION

The present invention is a novel process for preparation of epoxy resins containing triazine groups.

Epoxy resins containing triazine groups are known from Japan Kokai Tokkyo Koho No. 81 26,925 dated Mar. 16, 1981. However, the preparation of said resins involves the use of the difficult-to-obtain intermediate 2,4,6-trichloro-1,3,5-triazine. Furthermore, coupling of 2,4,6-trichloro-1,3,5-triazine with a diphenol through the chloride groups is difficult and leads to a relatively uncontrollable product mix.

The process of the present invention provides epoxy resins containing triazine groups using an easily prepared mixed cyanate of a diphenol. In the process, the polyphenol, such as 4,4'-isopropylidenediphenol (Bisphenol A) is reacted with less than a stoichiometric equivalent of a cyanogen chloride or bromide in the presence of a suitable base, such as triethylamine. This provides a mixture of monocyanate, dicyanate and, optionally, unreacted diphenol. Trimerization of this mixture provides hydroxyaromatic oligomers containing the triazine group. The oligomers and unreacted diphenol, if any, are then epoxidized using methods well known in the art.

A further benefit of the process of this invention is excellent control over the molecular weight (degree of polymerization) of the hydroxyaromatic oligomers containing triazine groups and thus the resulting molecular weight and therefore physical properties of the finished epoxy resin product. This is accomplished by varying the dicyanate (polycyanate) content of the diphenol (polyphenol) cyanate mixture used in the trimerization step of the process. A higher dicyanate content leads to higher molecular weight hydroxyaromatic oligomers through the presence of a greater number of bridged triazine groups. Conversely, a lower dicyanate content leads to lower molecular weight hydroxyaromatic oligomers.

Unreacted diphenol (polyphenol), which is preferably present, is converted to the corresponding diglycidyl ether during the epoxidation of the hydroxyaromatic oligomers. This improves overall processability of the epoxy resin. If desired, extra diphenol can be added prior to epoxidation to increase diphenol diglycidyl ether content of the finished epoxy resin product. Likewise, extra dicyanate may be added to the diphenol cyanate mixture prior to trimerization.

SUMMARY OF THE INVENTION

The present invention pertains to a process for preparing epoxy resins containing triazine groups which process comprises (I) reacting (A) at least one material having an average of more than one aromatic hydroxyl group per molecule with (B) at least 0.01 but not more than 0.95, preferably from about 0.05 to about 0.55, moles of cyanogen halide or mixture of cyanogen halides per aromatic hydroxyl group in the presence of (C) a suitable base in a quantity of from about 0.01 to about 1.1, preferably from about 0.05 to about 0.6, moles per aromatic hydroxyl group at a temperature and time sufficient to essentially complete the reaction and thereafter recovering the resultant cyanate mixture; (II) trimerizing the product resulting from (I) in the presence of a suitable trimerization catalyst at a temperature and time to essentially complete the trimerization reaction; (III) epoxidizing the resultant trimerized product from step (II) in a conventional manner by reaction with an epihalohydrin with subsequent dehydrohalogenation with a basic-acting material and finally recovering the resultant glycidyl ether product.

Another aspect of the present invention pertains to the cyanate mixtures prepared in step I above.

A further aspect of the present invention pertains to the epoxy resins prepared by the above described process.

Another aspect of the present invention pertains to the product resulting from curing a composition comprising the aforementioned epoxy resins and a curing quantity of a catalyst and/or curing agent therefor.

DETAILED DESCRIPTION OF THE INVENTION

Suitable materials having an average of more than one aromatic hydroxyl group per molecule which can be employed in the present invention include, for example, those represented by the formulas

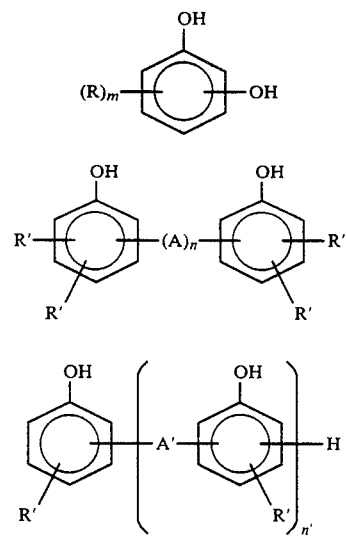

wherein A is a divalent hydrocarbon group having from 1 to about 12, preferably from about 1 to about 6 carbon atoms,

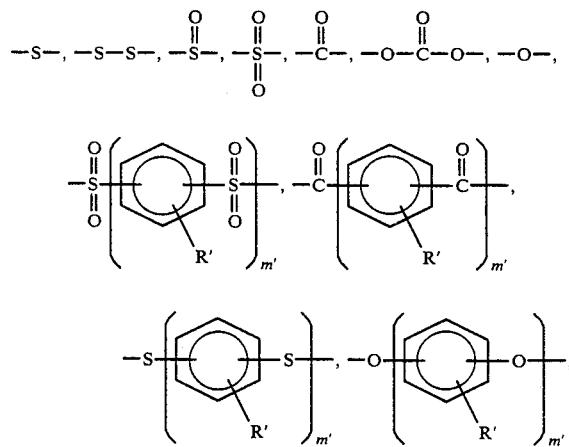

and the like; each A' is a divalent hydrocarbon group having from 1 to about 3, preferably 1, carbon atoms; each R is independently hydrogen, halogen, preferably chlorine or bromine, a hydrocarbyl group having from 1 to about 6 carbon atoms or a hydroxyl group; each R' is independently hydrogen or a hydrocarbyl group having from 1 to about 6 carbon atoms or a halogen, preferably chlorine or bromine; m has a value from zero to about 2; m' has a value from 1 to about 100; n has a value of zero or 1 and n' has a value from about 1.01 to about 6.

Particularly suitable aromatic hydroxyl-containing compounds include, for example, o-, m- and p-dihydroxybenzene, 2-tert butyl hydroquinone, 2,4-dimethyl resorcinol, 2,5-di-tert butyl hydroquinone, tetramethyl hydroquinone, 2,4,6-trimethyl resorcinol, 4-chlororesorcinol, 4-tert butyl pyrocatechol, 1,1-bis(4-hydroxyphenyl)ethane; 2,2-bis(4-hydroxyphenyl)propane; 2,2-bis(4-hydroxyphenyl)pentane; bis(4-hydroxyphenol)methane; 4,4'-dihydroxydiphenyl, 2,2'-dihydroxydiphenyl, 3,3',5,5'-tetramethyl-4,4'-dihydroxydiphenyl, 3,3',5,5'-tetrachloro-4,4'-dihydroxydiphenyl, 3,3',5,5'-tetrachloro-2,2'-dihydroxydiphenyl, 2,2',6,6'-tetrachloro-4,4'-dihydroxydiphenyl, 4,4'-bis((3-hydroxy)phenoxy)-diphenyl, 4,4'-bis((4-hydroxy)phenoxy)-diphenyl, 2,2'-dihydroxy-1,1'-binaphthyl, and other dihydroxydiphenyls; 4,4'-dihydroxydiphenyl ether, 3,3',5,5'-tetramethyl-4,4'-dihydroxydiphenyl ether, 3,3',5,5'-tetrachloro-4,4'-hydroxydiphenyl ether, 4,4'-bis(p-hydroxyphenoxy)-diphenyl ether, 4,4'-bis(p-hydroxyphenyl isopropyl)-diphenyl ether, 4,4'-bis(p-hydroxyphenoxy)-benzene, 4,4'-bis(p-hydroxyphenoxy)-diphenyl ether, 4,4'-bis(4-(4-hydroxyphenoxy)-phenyl sulfone)-diphenyl ether, and other dihydroxydiphenyl ethers; 4,4'-dihydroxydiphenyl sulfone, 3,3',5,5'-tetramethyl-4,4'-dihydroxydiphenyl sulfone, 3,3',5,5'-tetrachloro-4,4'-dihydroxydiphenyl sulfone, 4,4'-bis(p-hydroxyphenyl isopropyl)-diphenyl sulfone, 4,4'-bis((4-hydroxy)-phenoxy)-diphenyl sulfone, 4,4'-bis((3-hydroxy)phenoxy)-diphenyl sulfone, 4,4'-bis(4-(4-hydroxyphenylisopropyl)-phenoxy)-diphenyl sulfone, 4,4'-bis(4(4-hydroxy)diphenoxy)-diphenyl sulfone, and other diphenyl sulfones; 4,4'-dihydroxydiphenyl methane, 4,4'-bis(p-hydroxyphenyl)-diphenyl methane, 2,2-bis(p-hydroxyphenyl)-propane, 3,3',5,5'-tetramethyl-2,2'-bis(p-hydroxyphenyl)-propane, 3,3',5,5,'-tetrachloro-2,2-bis(p-hydroxyphenyl)-propane, 1,1-bis(p-hydroxyphenyl)-cyclohexane, bis-(2-hydroxy-1-naphthyl)-methane, 1,2-bis(p-hydroxyphenyl)-1,1,2,2-tetramethyl ethane, 4,4'-dihydroxybenzophenone, 4,4'-bis(4-hydroxy)phenoxy-benzophenone, 1,4-bis(p-hydroxyphenol isopropyl)-benzene, phloroglucinol, pyrogallol, 2,2',5,5'-tetrahydroxy-diphenyl sulfone, other dihydroxydiphenyl alkanes, mixtures thereof and the like.

Suitable cyanogen halides which can be employed herein include, for example, cyanogen chloride, cyanogen bromide, mixtures thereof and the like.

If desired, the method reported in Organic Syntheses, Vol. 61, page 35-37 (1983), published by John wiley & Sons, may be used to generate the required amount of cyanogen halide in situ, although this is less preferred than using neat cyanogen halide.

Suitable base materials which can be employed herein as component (I-C) include both inorganic bases and tertiary amines, such as, for example, sodium hydroxide, potassium hydroxide, triethylamine, mixtures thereof and the like. The tertiary amines are most preferred as the base material.

Suitable trimerization catalysts which can be employed herein include, for example, metal salts of carboxylic acids, such as, lead octoate, zince stearate, zinc acetylacetonate, at concentrations of about 0.001 to 5 percent. Most preferred catalysts are cobalt naphthenate and cobalt octoate, mixtures thereof and the like.

The epoxidation, step III, can be employed by the known methods described in *Handbook of Epoxy Resins* by Lee and Neville, McGraw-Hill, 1967 which is incorporated herein by reference. This usually includes reacting the product from step (II) with an epihalohydrin followed by dehydrohalogenation with a basic-acting material such as an alkali metal hydroxide and finally recovering the resultant glycidyl ether product.

Suitable curing agents and/or catalysts for the epoxy resins are described in the aforementioned *Handbook of Epoxy Resins*.

The step (I) reaction is usually conducted at a temperature of from about $-40°$ C. to about $60°$ C., preferably from about $-20°$ C. to about $25°$ C. for from about 10 minutes (600 s) to about 120 minutes (7200 s), preferably from about 10 minutes (600 s) to about 60 minutes (3600 s).

If desired, the reaction of step (I) can be conducted in the presence of an inert solvent reaction medium. Suitable such solvents include, for example, water, chlorinated hydrocarbons, ketones, mixtures thereof and the like.

The reaction of step (II) is usually conducted at a temperature of from about $70°$ C. to about $350°$ C., preferably from about $70°$ C. to about $200°$ C. for a period of from about 15 minutes (900 s) to about 120 minutes (7200 s), preferably from about 30 minutes (1800 s) to about 75 minutes (4500 s). The reaction is preferably performed in the presence of a suitable trimerization catalyst.

The epoxy resins of the present invention can be used to prepare, castings, coatings, laminates, encapsulations and the like, and are especially suited for use in high temperature environments.

The following examples are illustrative of the invention, but are not to be construed as to limiting the scope thereof in any manner.

EXAMPLE 1

A. Preparation of Diphenol Cyanate Mixture

Cyanogen bromide (1.10 moles, 116.52 grams) was added to a reactor containing stirred acetone (350 milliliter) under a nitrogen atmosphere. The cyanogen bromide-acetone solution was cooled to $-5°$ C., then bisphenol A (1.00 mole, 228.30 grams) dissolved in chilled acetone (650 milliliters) was added to the reactor. The stirred solution was allowed to equilibrate at $-5°$ C., then triethylamine (1.00 mole, 101.19 grams) was added to the reactor over a 74 minute (4200 s) period and so as to maintain the reaction temperature at $-5°$ C. After completion of the triethylamine addition, the reactor was maintained at $-5°$ C. for an additional 20 minutes (1200 s), followed by addition of the reaction product to chilled water (1 gallon) with agitation. After 1.5 hours (5400 s), the water and product mixture was subjected to multiple extractions with methylene chloride. The combined methylene chloride extracts were sequentially washed with dilute hydrochloric acid (5 percent), water, hydrochloric acid, water and then dried over anhydrous magnesium sulfate. The dry methylene chloride extract was filtered and solvent removed by rotary evaporation under vacuum. The resultant diphenol cyanate mixture was recovered (232.0 grams) as a transparent, viscous liquid. Infrared spectrophotometric analysis demonstrated the presence of the nitrile functionality as well as unreacted hydroxyl functionality. Liquid chromatographic analysis demonstrated the presence of 24.5 area percent bisphenol A, 54.1 area percent bisphenol A monocyanate, and 21.4 area percent bisphenol A dicyanate.

B. Trimerization of Diphenol Cyanate Mixture

A portion (200 grams) of the diphenol cyanate mixture from A above and 6.0 percent cobalt naphthenate (0.10 percent by weight, 0.20 gram) were thoroughly mixed and placed in a glass tray. The tray was then placed in a forced-air, convection-type oven and maintained for 1.0 hour (3600 s) at 177° C. The hydroxyaromatic oligomers containing triazine groups were recovered in quantitative yield as a transparent, brittle solid at room temperature (25° C.). The oligomers had a greenish-colored cast due to the catalyst. At the 177° C. temperature, the oligomers were still totally fluid. Infrared spectrophotometric analysis demonstrated essentially complete disappearance of the nitrile functionality, appearance of the triazine functionality, and the presence of unreacted hydroxyl functionality.

C. Epoxidation of Hydroxy Aromatic Oligomers Containing Triazine Groups

A portion (177.31 grams) of the hydroxyaromatic oligomers containing triazine groups from B above, epichlorohydrin (3.50 moles, 323.86 grams), isopropanol (35 percent by weight of epichlorohydrin used, 174.39 grams), and water (8 percent by weight of epichlorohydrin used, 28.16 grams) were added to a reactor and stirred under a nitrogen atmosphere at 75° C. until a solution was formed. At this time, the reactor was cooled to 50° C. and dropwise addition of a sodium hydroxide (1.56 moles, 50.4 grams) solution in water (201.6 grams) commenced and was completed over the next 45 minutes (2700 s). During this sodium hydroxide addition, the reaction temperature was allowed to increase to 60° C. and was then held at this temperature. Fifteen minutes (900 s) after the addition of sodium hydroxide solution, a second solution of sodium hydroxide (0.56 mole, 22.4 grams) in water (89.6 grams) was added dropwise to the reactor over the next 20 minutes (1200 s). Fifteen minutes (900 s) later, the reactor was cooled to 40° C. then an initial water wash (400 grams) was added to the reactor. The reactor contents were transferred to a separatory funnel containing additional epichlorohydrin (200 grams). The water wash layer was separated and discarded while the organic layer was added back into the separatory funnel along with a second water wash (600 grams). Epichlorohydrin (300 grams) was added to the separatory funnel then the water wash layer was separated and discarded. The organic layer was added back into the separatory funnel along with a final water wash (800 grams). Epichlorohydrin (500 grams) was added to the separatory funnel, then the water wash layer was separated and discarded. The recovered organic layer was stripped of solvents by rotary evaporation at 100° C. for 30 minutes (1800 s) under vacuum. The epoxy resin was recovered (209.1 grams) as a transparent, light amber-colored, tacky solid at room temperature (25° C.). Infrared spectrophotometric analysis demonstrated substantially complete disappearance of hydroxyl functionality, appearance of epoxide functionality and presence of triazine functionality. Epoxide titration revealed the presence of 16.85 percent by weight epoxide.

COMPARATIVE EXPERIMENT A

Direct epoxidation of the diphenol cyanate mixture of Example 1A was attempted as a potential route to epoxy resins containing triazine groups:

Diphenol cyanate mixture (202.64 grams) prepared using methods identical to that of Example 1A, epichlorohydrin (4.00 moles, 370.12 grams), isopropanol (35 percent by weight of epichlorohydrin used, 199.3 grams) and water (8 percent by weight of epichlorohydrin used, 32.18 grams) were added to a reactor and stirred under a nitrogen atmosphere with heating to 60° C. Dropwise addition of a sodium hydroxide (1.44 moles, 57.6 grams) solution in water (230.4 grams) commenced and was completed over the next 45 minutes (2700 s). During the sodium hydroxide addition, the reaction temperature was maintained at 60° C. Fifteen minutes (900 s) after the addition of the sodium hydroxide solution, a second solution of sodium hydroxide (0.64 mole, 25.6 grams) in water (102.4 grams) was added dropwise to the reactor over the next 20 minutes (1200 s). Fifteen minutes (900 s) later, the reactor was cooled to 30° C. then an initial water wash (400 grams) was added to the reactor. The reactor contents were transfered to a separatory funnel containing additional epichlorohydrin (200 grams). The water wash layer was separated and discarded while the organic layer was added back into the separatory funnel along with a second water wash (800 grams). Epchlorohydrin (400 grams) was added to the separatory funnel then the water wash layer was separated and discarded. The organic layer was added back into the separatory funnel along with a third water wash (800 grams). The water layer was separated and discarded. The recovered organic layer was stripped of solvents by rotary evaporation at 100° C. for 30 minutes (1800 s) under vacuum. The product was recovered (247.70 grams) as a transparent oil at room temperature (25° C.). Infrared spectrophotometric analysis demonstrated complete disappearance of the nitrile functionality and appearance of epoxide functionality. Epoxide titration revealed the presence of 16.55 percent by weight epoxide. Curing of the epoxy resin was not attempted since no nitrile groups were present to form triazine groups.

EXAMPLE 2

A. Preparation of Diphenol Cyanate Mixture

Cyanogen bromide (1.10 moles, 116.52 grams) was added to a reactor containing stirred acetone (350 milliliter) under a nitrogen atmosphere. The cyanogen bromide-acetone solution was cooled to −5° C., then bisphenol A (1.00 mole, 228.30 grams) dissolved in chilled acetone (650 milliliters) was added to the reactor. The stirred solution was allowed to equilibrate at −5° C., then triethylamine (1.00 mole, 101.19 grams) was added to the reactor over a 45 minute (2700 s) period and so as to maintain the reaction temperature at −2° to −5° C. After completion of the triethylamine addition, the reactor was maintained at −2° to 0° C. for an additional 20 minutes (1200 s), followed by addition of the reaction product to chilled water (1 gallon) with agitation. After 15 minutes (900 s), the water and product mixture was subjected to multiple extractions with methylene chloride. The combined methylene chloride extracts were sequentially washed with dilute hydrochloric acid (5 percent), water, hydrochloric acid, water and then dried over anhydrous magnesium sulfate. The dry methylene chloride extract was filtered and solvent removed by rotary evaporation under vacuum. The diphenol cyanate mixture was recovered (257.7 grams) as a transparent, viscous liquid. Infrared spectrophotometric analysis demonstrated the presence of the nitrile functionality as well as unreacted hydroxyl functionality. Liquid chromatographic analysis demonstrated the presence of 32.08 area percent bisphenol A, 46.69 area percent bisphenol A monocyanate, and 21.23 area percent bisphenol A dicyanate.

B. Trimerization of Diphenol Cyanate Mixture

The diphenol cyanate mixture (257.7 grams) from A above and 6.0 percent cobalt naphthenate (0.10 percent by weight, 0.26 gram) were thoroughly mixed and placed in a glass tray. The tray was then placed in a forced-air convection-type oven and maintained for 1.25 hours (4500 s) at 177° C. The hydroxyaromatic oligomers containing triazine groups were recovered in quantitative yield as a transparent, brittle solid at room temperature (25° C.). The oligomers had a greenish-colored cast due to the catalyst. At the 177° C. temperature, the oligomers were still totally fluid. Infrared spectrophotometric analysis demonstrated complete disappearance of the nitrile functionality, appearance of the triazine functionality, and the presence of unreacted hydroxyl functionality.

C. Epoxidation of Hydroxy Aromatic Oligomers Containing Triazine Groups

A portion (215.31 grams) of the hydroxyaromatic oligomers containing triazine groups from B above, epichlorohydrin (4.25 moles, 393.25 grams), isopropanol (35 percent by weight of epichlorohydrin used, 211.75 grams), and water (8 percent by weight of epichlorohydrin used, 34.20 grams) were added to a reactor and stirred under a nitrogen atmosphere at 75° C. until a solution was formed. At this time, the reactor was cooled to 50° C. and dropwise addition of a sodium hydroxide (1.53 moles, 61.2 grams) solution in water (244.8 grams) commenced and was completed over the next 45 minutes (2700 s). During this sodium hydroxide addition, the reaction temperature was allowed to increase to 60° C. and was then held at this temperature. Fifteen minutes (900 s) after the addition of sodium hydroxide solution, a second solution of sodium hydroxide (0.68 mole, 27.2 grams) in water (108.8 grams) was added dropwise to the reactor over the next 20 minutes (1200 s). Fifteen minutes (900 s) later, the reactor was cooled to 40° C. then an initial water wash (400 grams) was added to the reactor. The reactor contents were transferred to a separatory funnel containing additional epichlorohydrin (200 grams). The water wash layer was separated and discarded while the organic layer was added back into the separatory funnel along with a second water wash (200 grams). The organic layer was separated then added back into the separatory funnel along with a third water wash (200 grams). The water wash layer was separated and discarded while the organic layer was added back into the separatory funnel along with a final water wash (1000 grams). Epichlorohydrin (200 grams) was added to the separatory funnel, then the water wash layer was separated and discarded.

The recovered organic layer was stripped of solvents by rotary evaporation at 100° C. for 30 minutes (1800 s) under vacuum. The epoxy resin was recovered (287.8 grams) as a transparent, light amber-colored, solid at room temperature (25° C.). Infrared spectrophotometric analysis demonstrated substantially complete disappearance of hydroxyl functionality, appearance of epoxide functionality and presence of triazine functionality. Epoxide titration revealed the presence of 15.70 percent by weight epoxide.

EXAMPLE 3

A. Preparation of Diphenol Cyanate Mixture

Cyanogen bromide (0.55 moles, 58.26 grams) was added to a reactor containing stirred acetone (175 milliliters) under a nitrogen atmosphere. The cyanogen bromide-acetone solution was cooled to −5° C., then bisphenol A (1.00 mole, 228.30 grams) dissolved in chilled acetone (650 milliliters) was added to the reactor. The stirred solution was allowed to equilibrate at −5° C., then triethylamine (0.50 mole, 50.60 grams) was added to the reactor over a 25 minute (1500 s) period and so as to maintain the reaction temperature at −2° to −5° C. After completion of the triethylamine addition, the reactor was maintained at −2° to 0° C. for an additional 20 minutes (1200 s), followed by addition of the reaction product to chilled water (1 gallon) with agitation. After 15 minutes (900 s), the water and product mixture was subjected to multiple extractions with methylene chloride. The combined methylene chloride extracts were sequentially washed with dilute hydrochloric acid (5 percent), water, hydrochloric acid, water and then dried over anhydrous magnesium sulfate. The dry methylene chloride extract was filtered and solvent removed by rotary evaporation under vacuum. The diphenol cyanate mixture was recovered (229.7 grams) as a white-colored solid at room temperature (25° C.). Infrared spectrophotometric analysis demonstrated the presence of the nitrile functionality as well as unreacted hydroxyl functionality. Liquid chromatographic analysis demonstrated the presence of 55.82 area percent bisphenol A, 37.89 area percent bisphenol A monocyanate, and 6.29 area percent bisphenol A dicyanate.

B. Trimerization of Diphenol Cyanate Mixture

The diphenol cyanate mixture (229.7 grams) from A above and 6.0 percent cobalt naphthenate (0.10 percent by weight, 0.23 gram) were thoroughly mixed and placed in a glass tray. The tray was then placed in a forced-air, convection-type oven and maintained for 1.25 hour (4500 s) at 177° C. The hydroxyaromatic oligomers containing triazine groups were recovered in quantitative yield as a transparent, brittle solid at room temperature (25° C.). The oligomers had a greenish-colored cast due to the catalyst. At the 177° C. temperature, the oligomers were still totally fluid. Infrared spectrophotometric analysis demonstrated complete disappearance of the nitrile functionality, appearance of the triazine functionality, and the presence of unreacted hydroxyl functionality.

C. Epoxidation of Hydroxy Aromatic Oligomers Containing Triazine Groups

A portion (215.00 grams) of the hydroxyaromatic oligomers containing triazine groups from B above, epichlorohydrin (6.865 moles, 635.22 grams), isopropanol (35 percent by weight of epichlorohydrin used, 342.04 grams), and water (8 percent by weight of epichlorohydrin used, 55.24 grams) were added to a reactor and stirred under a nitrogen atmosphere at 60° C. until a solution was formed. At this time, the reactor was cooled to 50° C. and dropwise addition of a sodium hydroxide (2.4714 moles, 98.86 grams) solution in water (395.42 grams) commenced and was completed over the next 45 minutes (2700 s). During this sodium hydroxide addition, the reaction temperature was allowed to increase to 60° C. and was then held at this temperature. Fifteen minutes (900 s) after the addition of sodium hydroxide solution, a second solution of sodium hydroxide (1.0984 mole, 43.94 grams) in water (175.76 grams) was added dropwise to the reactor over the next 20 minutes (1200 s). Fifteen minutes (900 s) later, the reactor was cooled to 40° C. then an initial water wash (400 grams) was added to the reactor. The reactor contents were transferred to a separatory funnel containing additional epichlorohydrin (200 grams). The water wash layer was separated and discarded while the organic layer was added back into the separatory funnel along with a second water wash (200 grams). The organic layer was separated then added back into the separatory funnel along with a third water wash (200 grams). The water wash layer was separated and discarded while the organic layer was added back into the separatory funnel with a final water wash (1000 grams). Epichlorohydrin (200 grams) was added to the separatory funnel, then the water wash layer was separated and discarded. The recovered organic layer was stripped of solvents by rotary evaporation at 100° C. for 30 minutes (1800 s) under vacuum. The epoxy resin was recovered (272.4 grams) as a transparent, light yellow-colored liquid at room temperature (25° C.). Infrared spectrophotometric analysis demonstrated substantially complete disappearance of hydroxyl functionality, appearance of epoxide functionality and presence of triazine functionality. Epoxide titration revealed the presence of 21.55 percent by weight epoxide.

EXAMPLE 4

A portion of the epoxy resin of Example 3C (265.00 grams) was heated to 75° C. then methylenedianiline (65.74 grams) was added and thoroughly mixed in. This solution was used to prepare a clear, unfilled 1/8 inch (0.3175 cm) casting for heat distortion temperature (264 psi, 1820 kPa), tensile and flexural strength, flexural modulus, percent elongation, average Barcol hardness (934-1 scale) and unnotched Izod impact strength determinations. The casting was cured for 2 hours (7200 s) at 75° C. followed by post curing of 2 hours (7200 s) at 125° C., 2 hours (7200 s) at 175° C., then 2 hours (7200 s) at 200° C. Mechanical properties of tensile (8) and flexural (5) test pieces were determined using an Instron machine with standard test methods (ASTM D-638 and D-790). Heat distortion temperature of clear casting test pieces (2) was determined using an Aminco Plastic Deflection Tester (American Instrument Co.) with standard test methods (ASTM D-648 modified). Nine 2.5 by 0.5 by 0.125 inch (6.35 by 1.27 by 0.3125 cm) test pieces were prepared from the clear, unfilled casting and tested for unnotched Izod impact using a TMI Impact Tester No. 43-1 with standard test methods (ASTM D-256). The results are reported in Table I.

TABLE I

| Average Barcol Hardness | 42 |
| Heat Distortion Temperature | 307/152.75 |

TABLE I-continued

| °F./°C. | | |
|---|---|---|
| Tensile strength, | psi | 10,694 |
| | kPa | 73,733 |
| Elongation (%) | | 3.69 |
| Flexural Strength, | psi | 21,709 |
| | kPa | 149,679 |
| Flexural Modulus, | psi | 519,000 |
| | kPa | 3,578,401 |
| Izod Impact Strength unnotched | | |
| ft-lbs/in. | | 8.24 |
| J/cm | | 4.398 |

EXAMPLE 5

The hydroxyaromatic oligomers containing triazine groups from Examples 1B and 3B were analyzed by gel permeation chromatography using polystyrene standards. The results are reported in Table II.

TABLE II

| | Average Molecular Weight | Polydispersity Ratio |
|---|---|---|
| Example 1B | 13,589 | 2.57 |
| Example 3B | 3,748 | 1.40 |

EXAMPLE 6

A sample (7.60 milligrams) of the clear, unfilled casting of Example 4 was analyzed by differential scanning calorimetry (DSC) under a nitrogen atmosphere using a scan rate of 10° C. per minute. A pair of glass transition temperatures (Tg) were observed at 165° C. and 310° C. while the onset of endothermic decomposition occurred at 380° C.

EXAMPLE 7

A sample (14.98 milligrams) of the clear, unfilled casting of Example 4 was analyzed by thermogravimetric analysis (TGA) using a nitrogen flow rate of 80 cubic centimeters per minute and a rate of temperature increase of 10° C. per minute. The weight of the sample as a function of temperature is reported in Table III.

TABLE III

| Temperature (°C.) | Percent of Original Weight |
|---|---|
| 200 | 99.6 |
| 250 | 99.2 |
| 300 | 98.9 |
| 350 | 97.0 |
| 400 | 66.8 |
| 450 | 31.4 |
| 500 | 24.8 |

EXAMPLE 8

Dynamic mechanical spectrometry (DMS) was completed using a sample of the clear, unfilled casting of Example 4. The sample dimensions were 44.8 millimeters in length, 3.6 millimeters in thickness and 13.0 millimeters in width. The sample was loaded and run with a strain of 0.05 percent and a frequency of one hertz in a nitrogen atmosphere from −160° to 400° C. using a Rheometrics model 605 mechanical spectrometer. The DMS analysis revealed a drop in storage modulus at 150° C. indicating a glass transition, an increase in storage modulus after 190° C. as expected for the rubbery state followed by a second drop in storage modulus at 290° C. indicating a second glass transition.

I claim:

1. A process for preparing epoxy resins containing triazine groups which process comprises (I) reacting (A) at least one material having an average of more than one aromatic hydroxyl group per molecule with (B) at least 0.01 but not more than 0.95 moles of cyanogen halide or mixture of cyanogen halides per aromatic hydroxyl group in the presence of (C) a suitable base in a quantity of from about 0.01 to about 1.1 moles per aromatic hydroxyl group at a temperature and time sufficient to essentially complete the reaction and thereafter recovering the resultant cyanate mixture; (II) trimerizing the product resulting from (I) in the presence of a suitable trimerization catalyst at a temperature and time to essentially complete the trimerization reaction; (III) epoxidizing the resultant trimerized product from step (II) in a conventional manner by reaction with an epihalohydrin with subsequent dehydrohalogenation with a basic-acting material and finally recovering the resultant glycidyl ether product.

2. A process of claim 1 wherein
   (i) the ratio of aromatic hydroxyl groups contained in (A):moles of (B):moles of (C) is from about 1:0.05:0.05 to about 1:0.55:0.60;
   (ii) step (I) is conducted at a temperature of from about −40° C. to about 60° C. for from about 10 minutes to about 120 minutes; and
   (iii) step (II) is conducted at a temperature of from about 70° C. to about 350° C. for from about 15 minutes to about 120 minutes.

3. A process of claim 2 wherein
   (i) step (I) is conducted at a temperature of from about −20° C. to about 25° C. for from about 10 minutes to about 60 minutes; and
   (ii) step (II) is conducted at a temperature of from about 70° C. to about 200° C. for from about 30 minutes to about 75 minutes.

4. A process of claim 1 wherein
   (i) said cyanogen halide is cyanogen bromide;
   (ii) said material having an average of more than one aromatic hydroxyl group per molecule is a bisphenol;
   (iii) said suitable base is a tertiary amine;
   (iv) said trimerization catalyst is a metal salt of a carboxylic acid;
   (v) said epihalohydrin is epichlorohydrin; and
   (vi) said basic acting material is an alkali metal hydroxide.

5. A process of claim 4 wherein
   (i) said material having an average of more than one aromatic hydroxyl group per molecule is bisphenol A;
   (ii) said suitable base is triethylamine;
   (iii) said trimerization catalyst is cobalt naphthenate; and
   (iv) said basic-acting material is sodium hydroxide.

6. A process of claim 3 wherein
   (i) said cyanogen halide is cyanogen bromide;
   (ii) said material having an average of more than one aromatic hydroxyl group per molecule is a bisphenol;
   (iii) said suitable base is a tertiary amine;
   (iv) said trimerization catalyst is a metal salt of a carboxylic acid;
   (v) said epihalohydrin is epichlorohydrin; and
   (vi) said basic acting material is an alkali metal hydroxide.

7. A process of claim 6 wherein
   (i) said material having an average of more than one aromatic hdyroxyl group per molecule is bisphenol A;
   (ii) said suitable base is triethylamine;
   (iii) said trimerization catalyst is cobalt naphthenate; and
   (iv) said basic-acting material is sodium hydroxide.

8. A process of claim 3 wherein
   (i) said cyanogen halide is cyanogen bromide;
   (ii) said material having an average of more than one aromatic hdyroxyl group per molecule is a bisphenol;
   (iii) said suitable base is a tertiary amine;
   (iv) said trimerization catalyst is a metal salt of a carboxylic acid;
   (v) said epihalohydrin is epichlorohydrin; and
   (vi) said basic acting material is an alkali metal hydroxide.

9. A process of claim 8 wherein
   (i) said material having an average of more than one aromatic hydroxyl group per molecule is bisphenol A;
   (ii) said suitable base is triethylamine;
   (iii) said trimerization catalyst is cobalt naphthenate; and
   (iv) said basic-acting material is sodium hydroxide.

10. A cyanate mixture resulting from reacting (A) at least one material having an average of more than one aromatic hydroxyl group per molecule with (B) at least 0.01 but not more than 0.95 moles of cyanogen halide or mixture of cyanogen halides per aromatic hydroxyl group in the presence of (C) a suitable base in a quantity of from about 0.01 to about 1.1 moles per aromatic hydroxyl group at a temperature and time sufficient to essentially complete the reaction and thereafter recovering the resultant cyanate mixture.

11. A cyanate mixture of claim 10 wherein
    (i) the ratio of aromatic hydroxyl groups contained in (A):moles of (B):moles of (C) is from about 1:0.05:0.05 to about 1:0.55:0.60; and
    (ii) the reaction is conducted at a temperature of from about −40° C. to about 60° C. for from about 10 minutes to about 120 minutes.

12. A cyanate mixture of claim 11 wherein the reaction is conducted at a temperature of from about −20° C. to about 25° C. for from about 10 minutes to about 60 minutes.

13. A cyanate mixture of claim 10 wherein
    (i) said cyanogen halide is cyanogen bromide;
    (ii) said material having an average of more than one aromatic hydroxyl group per molecule is a bisphenol; and
    (iii) said suitable base is a tertiary amine.

14. A cyanate mixture of claim 13 wherein
    (i) said material having an average of more than one aromatic hydroxyl group per molecule is bisphenol A; and
    (ii) said suitable base is triethylamine.

15. A cyanate mixture of claim 11 wherein
    (i) said cyanogen halide is cyanogen bromide;
    (ii) said material having an average of more than one aromatic hydroxyl group per molecule is a bisphenol; and
    (iii) said suitable base is a tertiary amine.

16. A cyanate mixture of claim 15 wherein
    (i) said material having an average of more than one aromatic hydroxyl group per molecule is bisphenol A; and (ii) said suitable base is triethylamine.

17. A cyanate mixture of claim 12 wherein
(i) said cyanogen halide is cyanogen bromide;
(ii) said material having an average of more than one aromatic hydroxyl group per molecule is a bisphenol; and
(iii) said suitable base is a tertiary amine.

18. A cyanate mixture of claim 17 wherein
(i) said material having an average of more than one aromatic hydroxyl group per molecule is bisphenol A; and
(ii) said suitable base is triethylamine.

19. An epoxy resin prepared by the process of claim 1.

20. An epoxy resin prepared by the process of claim 2.

21. An epoxy resin prepared by the process of claim 3.

22. An epoxy resin prepared by the process of claim 4.

23. An epoxy resin prepared by the process of claim 5.

24. An epoxy resin prepared by the process of claim 6.

25. An epoxy resin prepared by the process of claim 7.

26. An epoxy resin prepared by the process of claim 8.

27. An epoxy resin prepared by the process of claim 9.

28. A product resulting from curing an epoxy resin of claim 19 with a curing quantity of a suitable catalyst and/or curing agent.

29. A product resulting from curing an epoxy resin of claim 20 with a curing quantity of a suitable catalyst and/or curing agent.

30. A product resulting from curing an epoxy resin of claim 21 with a curing quantity of a suitable catalyst and/or curing agent.

31. A product resulting from curing an epoxy resin of claim 22 with a curing quantity of a suitable catalyst and/or curing agent.

32. A product resulting from curing an epoxy resin of claim 23 with a curing quantity of a suitable catalyst and/or curing agent.

33. A product resulting from curing an epoxy resin of claim 24 with a curing quantity of a suitable catalyst and/or curing agent.

34. A product resulting from curing an epoxy resin of claim 25 with a curing quantity of a suitable catalyst and/or curing agent.

35. A product resulting from curing an epoxy resin of claim 26 with a curing quantity of a suitable catalyst and/or curing agent.

36. A product resulting from curing an epoxy resin of claim 27 with a curing quantity of a suitable catalyst and/or curing agent.

* * * * *